United States Patent [19]
Henderson et al.

[11] Patent Number: 5,399,979
[45] Date of Patent: Mar. 21, 1995

[54] CAPACITANCE PROBE ASSEMBLY

[75] Inventors: Richard W. Henderson, Edmonton; Richard W. Thornton, Calgary, both of Canada

[73] Assignee: 342975 Alberta Ltd., Edmonton, Canada

[21] Appl. No.: 231,633

[22] Filed: Apr. 23, 1993

Related U.S. Application Data

[63] Continuation-in-part of Ser. No. 372,011, Jun. 27, 1989, abandoned.

[51] Int. Cl.⁶ .......................................... G01R 27/26
[52] U.S. Cl. .............................. 324/677; 324/603; 324/667; 324/674; 324/681; 324/690; 73/304 C; 73/172; 331/49
[58] Field of Search ............... 340/620; 73/172, 304 C; 331/56, 49; 324/603, 609, 664, 667, 674, 677, 689, 690

[56] References Cited

U.S. PATENT DOCUMENTS

| | | | |
|---|---|---|---|
| 3,723,899 | 3/1973 | McClaskey | 331/49 |
| 3,931,610 | 1/1976 | Marin | 324/678 |
| 4,003,259 | 1/1977 | Hope | 73/304 C |
| 4,182,981 | 1/1980 | Shum | 73/172 |
| 4,190,797 | 2/1980 | Lecklider | 73/172 |
| 4,350,040 | 9/1982 | Fasching | 73/304 C |
| 4,373,390 | 2/1983 | VanDyke | 73/304 C |
| 4,611,489 | 9/1986 | Spaargaren | 73/304 C |
| 4,737,706 | 4/1988 | Eilersen | 324/678 |
| 4,965,523 | 10/1990 | Baker | 324/671 |
| 4,996,658 | 2/1991 | Baker | 324/671 |
| 5,097,216 | 3/1992 | Dimmick | 324/690 |

*Primary Examiner*—Kenneth A. Wieder
*Assistant Examiner*—Jose M. Solis
*Attorney, Agent, or Firm*—Millen, White, Zelano, & Branigan

[57] ABSTRACT

The assembly comprises an electrically insulated linear array of a plurality of active plates working in conjunction with common return plate means to provide a line of capacitors. The electrically insulated active plate array and common return plate means extend through a column of multi-phase fluid. A discrete oscillator circuit is positioned adjacent to and is permanently connected to each active plate for charging and discharging it. Means are provided for sequentially enabling the oscillator circuits to produce signals which are each indicative of the dielectric constant of the thin horizontal slice of fluid extending between the active plate and the return plate means. The signals are collected by a microprocessor which analyzes them to provide a dielectric constant profile of the fluid column. Interfaces of phases can be located from the profile and the composition of the fluid phases can be determined.

4 Claims, 4 Drawing Sheets

CAPACITANCE PROBE ASSEMBLY

This application is a continuation-in-part of application Ser. No. 07/372,011, filed Jun. 27, 1989, now abandoned.

FIELD OF THE INVENTION

The present invention relates to a probe of the capacitance type. The probe is useful in connection with determining the positions of interfaces in a multi-phase fluid column and determining the proportions of components making up a gassy oil-water emulsion. The invention includes novel methods based on capacitance measurements.

BACKGROUND OF THE INVENTION

The present invention was conceived in connection with monitoring the oil, water and gas production of wells involved in an oilfield thermal recovery project. While the scope of the invention is not limited to that environment, as is made clearer below, it is appropriate to begin by addressing the problems associated with such monitoring.

Thermal processes are commonly employed in recovering oil from oil field reservoirs containing heavy, viscous oil. By introducing heat into the reservoir, the viscosity of the oil is reduced, so that its mobility is greater and it can more easily be produced. In some of these processes, steam is injected into the reservoir. In others, combustion is initiated in the reservoir adjacent an injection well; air is then injected through the well to maintain the combustion and cause a fire front to slowly advance toward a production well. In both cases a pressure drive is applied to force fluids toward the production well, through which they are produced.

The production streams issuing from the wells are multi-phase in nature. They normally comprise oil, water and gases. The relative quantities of these components of the production stream vary over time, sometimes markedly and quickly.

For a variety of reasons, well operators need to be able to accurately determine, on an on-going basis, the relative proportions and the mass rates of each of the oil, water and gas. However, this is not easily accomplished.

If one retains a batch of produced fluid in a tank, free water will readily settle out and form a discrete layer. The height of the layer can be determined with a tape gauge and the volume and mass calculated. Also, most of the free gas will break out and leave the tank through an overhead line. The flow rate of this gas stream can accurately be determined using a conventional flow meter.

After the free gas separation, there remains an intermediate layer containing oil, gas and water in an emulsified form. The components of the emulsion do not readily separate to facilitate their measurement. To further complicate the matter, the relative quantities of the components vary significantly with time, making it desirable to monitor their proportions on a virtually continuous basis if any reasonable deg.ree of accuracy is required.

In actual oilfield practice, the most commonly applied technique for establishing the composition of the emulsion involves taking grab samples and centrifuging them to ascertain the "cuts" or proportions of the components.

However, there are problems associated with sampling, including:

sampling is often non-representative and therefore inaccurate;

the procedure is commonly practiced manually and thus there will typically be a time lag between taking the sample and having the readings in hand.

There has therefore long existed a need for an in-line assembly that could automatically, virtually continuously and accurately establish:

the cuts of oil, water and gas making up the emulsion; and the mass flow rates of the components.

As a first step in this direction, the present assignee has developed a metering separator capable of monitoring the mass flow rate of the liquid contained in an oilfield production stream. This separator is described in U.S. Pat. No. 4,549,432.

In connection with this separator, the in-coming feed stream is delivered tangentially into the vessel, so that the fluid is caused to swirl. Most of the gas breaks out, forms a central vortex, and leaves the vessel chamber through an overhead outlet line. The flow rate through this line is measured with a meter. The remaining fluid is temporarily retained as a batch in the vessel chamber. Free water quickly settles and forms a bottom layer. A layer of gassy water-in-oil emulsion accumulates above the free water. Together these bottom two layers form a liquid-containing column. The free gas, of course, forms a third layer above the column. A differential pressure transducer is used to monitor the accumulating head of the column. The time taken to accumulate the batch is also measured. When the head reaches a predetermined value, control means close a fill valve, open a dump valve and the batch is quickly discharged from the vessel. Back-pressure is maintained on the gas outlet line to push the fluid out during dumping. The signal from the differential pressure transducer initiates closure of the dump valve when the head reaches a predetermined low. A microprocessor keeps track of the number of dumps and calculates the mass flow rate of the liquid passing through the unit, by using the head measurement, the time measurements, and the known internal cross-section area of the separator.

However, up until the development of the present invention, the relative cuts of the components in the dumped column were determined by sampling, accompanied with the shortcomings previously referred to.

Thus the development of the present invention was initiated to attain the end of being able to automatically establish, for a batch, the heights of each of the free water and emulsion layers and the cuts of water, oil and gas forming the emulsion. With this information, taken in conjunction with other known information, specifically the cross-sectional area of the vessel chamber and the known specific gravity of the components, it would be possible to compute the mass flow rates of each of the oil, water and gas.

The present system incorporates the use of capacitance to establish a measure of the dielectric constant of the fluid extending between plates. When the fluid between the plates is an emulsion, the measured capacitance will vary depending upon the relative proportions of the emulsion components. Generally, capacitive devices have heretofore been used in oilfield applications for establishing oil/water ratios in conjunction with a two component fluid. To our knowledge, few systems cope with the presence of a third component, gas, in the emulsion. One such system, described in U.S. Pat. No. 4,289,020 issued to PAAT, used a nuclear device to determine the density of an emulsion. This measurement enabled the associated apparatus to calculate the oil/water ratio of the emulsion. But it is expected that this device cannot cope with free water. In addition, capacitive devices have been disclosed in the prior art for the purpose of locating interfaces in a two phase column of fluid (e.g. see U.S. Pat. No. 4,503,383, issued to Agar).

SUMMARY OF THE INVENTION

In accordance with the preferred form of the present invention, a novel two terminal capacitance probe assembly is provided, which may be combined with the aforementioned metering separator.

As previously described, the metering separator comprises:

- a vessel which is adapted to receive an incoming feedstock, comprising oil, gas and water in single phase and emulsion form and has outlet lines for producing an overhead gas product and an underflow liquid-containing product;
- means associated with the vessel for causing centrifugal and gravity separation of the feedstock components into gas, emulsion and free water layers, which are temporarily retained as a batch;
- means for measuring, for the batch, the mass of the column consisting of the free water and emulsion layers;
- means for measuring the time taken to accumulate the batches; and,
- means for measuring the overhead gas component production rate.

The capacitance probe assembly, which is used in conjunction with, for example, the separator, comprises:

- a common return plate means (which can be the wall of the vessel) which is associated with a generally linear array of discrete active plates. The active plates are electrically insulated from each other and the feedstock, preferably by enclosing them in an electrically insulating closed tubular shell, and are arranged so as to be capacitively coupled with the return plate means by the fluid extending between them;
- the linear array of electrically insulated plates is adapted to extend vertically in the column of fluid through a vertical interval which will be intersected by each of the gas/emulsion and emulsion/free-water interfaces;
- the assembly further includes: (1) means for directly charging and discharging each of the active plates individually, so that the frequency of the applied potential varies with the dielectric constant of the fluid extending between the active plate involved, which is a first terminal, and the return plate means, which is the second terminal, and producing variable frequency signals indicative of said dielectric constant; and (2) means for collecting the individual signals resulting from the activation of the plates and determining for each such signal a value indicative of the dielectric constant of the fluid extending between the active plate involved and the return plate means. More specifically, the means for individually charging and discharging the plates comprises: a plurality of discrete oscillator circuits, equal in number to the Number of active plates and each positioned on or adjacent to (collectively referred to as "close to") an associated active plate, and means, such as parallel shift registers, for selectively and sequentially enabling the permanently connected oscillator circuits. The frequency signals produced by the individual oscillating circuits are measured and analyzed by a microprocessor.

The system as just described involves a number of features and yields certain information of interest, namely:

- the capacitance probe assembly involves a multiplicity of linearly arranged active plates, each of which, when electronically activated, cooperates with the return plate means to produce frequency signals indicative of the dielectric constant of the thin slice of fluid extending between them. The microprocessor measures the so-produced individual signals and compares them, to locate the height. levels at which the values diverge from specific values derived from the known fluid components, thereby indicating an interface. Stated otherwise, the system involves using a vertical line of capacitors, operating individually, to establish a dielectric constant profile of the vessel contents to thereby identify and locate the free water/emulsion and emulsion/gas interfaces. With this information, the vertical extent of the free water and vertical extent of the emulsion layers can be determined. Since the cross-sectional area of the vessel chamber is known, the volumes of each of the two liquid-containing layers can be determined;
- the system further includes means for measuring the total mass of the liquid-containing column formed by the batch. Since the specific gravity of the free water is known and the height and cross-sectional area of the free water layer are now known, the mass of the free water layer can be determined, thereby yielding the mass of the emulsion layer by subtraction. As the mass and volume of the emulsion layer are now known, a value indicative of the specific gravity of the emulsion can be determined;
- the capacitance values derived from the emulsion can now be compared against previously assembled capacitance data for known ratios of the water in oil emulsion. Comparison of the emulsion values against the reference data will yield the approximate oil/water ratio of the emulsion and permit of calculation of the approximate water volume ratio.
- using the approximate volume ratio of water, the volume of gas in the emulsion can be computed. With the recomputed values, accurate values of the mass of water and mass of oil in the emulsion can be determined.

It will be noted that the probe assembly involves a linear array of a multiplicity of active plates. This feature allows the presence and position of more than one interface to be detected. It also increases the accuracy of the probe. Since it enables vertical sectioning of the vessel contents, this permits the electronic interrogation of each horizontal "slice" of the fluid column, thereby providing enablement for determining the location of interfaces and determining the true oil/water ratio for the entire emulsion layer.

It will further be noted that the probe assembly preferably involves a plurality of discrete oscillator circuits mounted within the insulating shell, each such oscillator circuit being positioned on or adjacent to its associated active plate. This feature is incorporated to ensure that the ratio of the change in plate capacitance (due to feed stock changes) to parasitic capacitance is large, further improving system resolution. Since changes in parasitic capacitance do occur and the instrumentation cannot discriminate changes in parasitic capacitance from changes in plate capacitance, a low plate to parasitic capacitance ratio can lead to reduced accuracy. The location and selection of the circuitry disclosed are chosen to increase the ratio of plate capacitance to parasitic capacitance .by reducing the lead length from the actuating electronics to the active plates. This reduction in lead length serves to reduce the total parasitic capacitance, thereby increasing the plate to parasitic capacitance ratio.

The invention has been summarized in connection with the specific and preferred case of the capacitive assembly working in conjunction with the metering separator, to yield interface height and dielectric constant information which can be used to calculate mass flow rates for an oilfield production stream. However, it is to be understood that the capacitive assembly is itself unique and can be used in other applications, such as monitoring only interface levels in a tank or establishing cuts in a body of fluid. In addition, the processes inherent in its use have novelty. These various aspects. of the assembly are within the scope of the invention and are broadly describable as follows:

In one broad aspect, the invention comprises a two terminal type capacitance probe assembly adapted to be capacitively coupled with a return plate means by fluid with which the assembly and the return plate means are placed in contact, comprising: (a) a generally linear array of discrete active plates mounted within an electrically insulating shell so that the plates are electrically insulated from the fluid; (b) a plurality of discrete oscillator circuits; (c) means for energizing the oscillator circuits; (d) each oscillator circuit being individually and permanently connected to an active plate for directly charging and discharging that active plate so that the frequency of the applied potential varies with the dielectric constant of the fluid extending between that active plate, which is a first terminal of the assembly, and the return plate means, which is the second terminal, to produce variable frequency signals indicative of said dielectric constant; (e) means for selectively and individually enabling an oscillator circuit; and (f) means for collecting the individual signals produced by the oscillator circuits and determining for each signal a value indicative of the dielectric constant of the fluid extending between the active plate involved and the return plate means.

In another broad aspect, the invention comprises a capacitive assembly for establishing individual values indicative of dielectric constant for multiple transverse sections of a column of fluid, to enable development of a profile of the dielectric constant of the column, comprising: a common return plate; a generally linear array of discrete active plates, each active plate being electrically insulated from the fluid and being adapted to be capacitively coupled to the return plate by the transverse section of fluid extending between them; said return plate and linear array being of sufficient length to extend the length of the fluid column to be examined; means for charging and discharging the active plates individually and producing signals which are indicative of the dielectric constant of the fluid extending between the active plate involved and the return plate means; and means for collecting the individual signals and obtaining for each such signal a value indicative of the dielectric constant of the fluid extending between the active plate involved and the return plate.

In another broad aspect, the invention is a method for establishing measures which enable a calculation of the positions of interfaces of each of the free water/emulsion and emulsion/gas in a batch of a stream comprising oil, water and gas, comprising: temporarily retaining the batch in a vessel to form a top layer of gas and a column consisting of a bottom layer of free water and an intermediate layer of gassy water-in-oil emulsions measuring the head of the column of free water and emulsion; measuring dielectric values of multiple discrete horizontal fluid sections of the layers along a vertical interval traversing the free water/emulsion and emulsion/gas interfaces; and comparing the dielectric values obtained to determine the locations of the interfaces.

DESCRIPTION OF THE PREFERRED EMBODIMENT

The Figures show an embodiment of the invention which is adapted to both identify interfaces and determine their height in a multi-phase batch of fluid and to establish an inventory of the batch. More particularly, the embodiment comprises a metering separator A and a capacitance probe assembly B working together to yield useful information which is processed by a microprocessor C, forming part of the assembly B, for the calculation of mass rates of the batch components.

Figure 1:
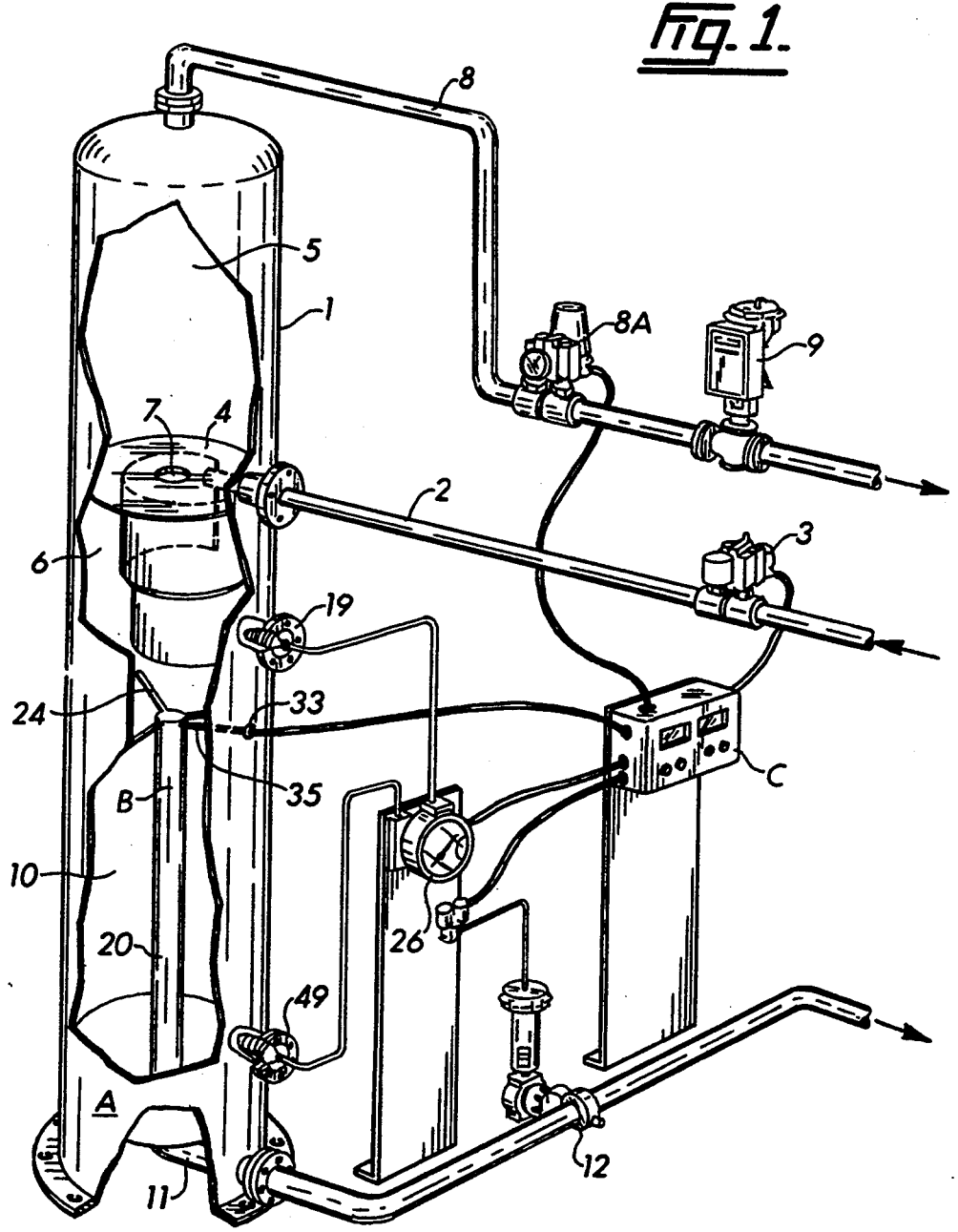
FIG. 1 is a perspective, partly-broken-away view showing the separator with the capacitance probe assembly in operating position in the separator.

As shown in FIG. 1, the separator A comprises a vertical vessel 1 having a tangentially arranged feed line 2 opening into its upper end. Flow into the vessel 1 through the line 2 is controlled by a valve 3. The feed line 2 delivers the oilwell production stream into an involute inlet housing 4, mounted within the vessel chamber 5. The housing 4 has a side-opening fluid outlet 6 and a top-opening gas outlet 7. The production stream entering the housing 4 swirls and forms an inner gas vortex and an outer liquid layer containing entrained gas. The outer fluid layer leaves the housing 4 through the outlet 7. The gas moves out of the vessel chamber 5 through overhead line 8. A meter 8a in line 8 measures the gas flow and supplies signals indicative thereof to the microprocessor C. A backpressure valve 9 maintains a pre-determined back pressure in the vessel chamber 5, for flushing out the batch 10, when it is to be dumped. The liquid-containing fluid can leave the vessel chamber 5 through an underflow line 11. Flow through the underflow line 11 is controlled by a dump valve 12.

Figure 2:
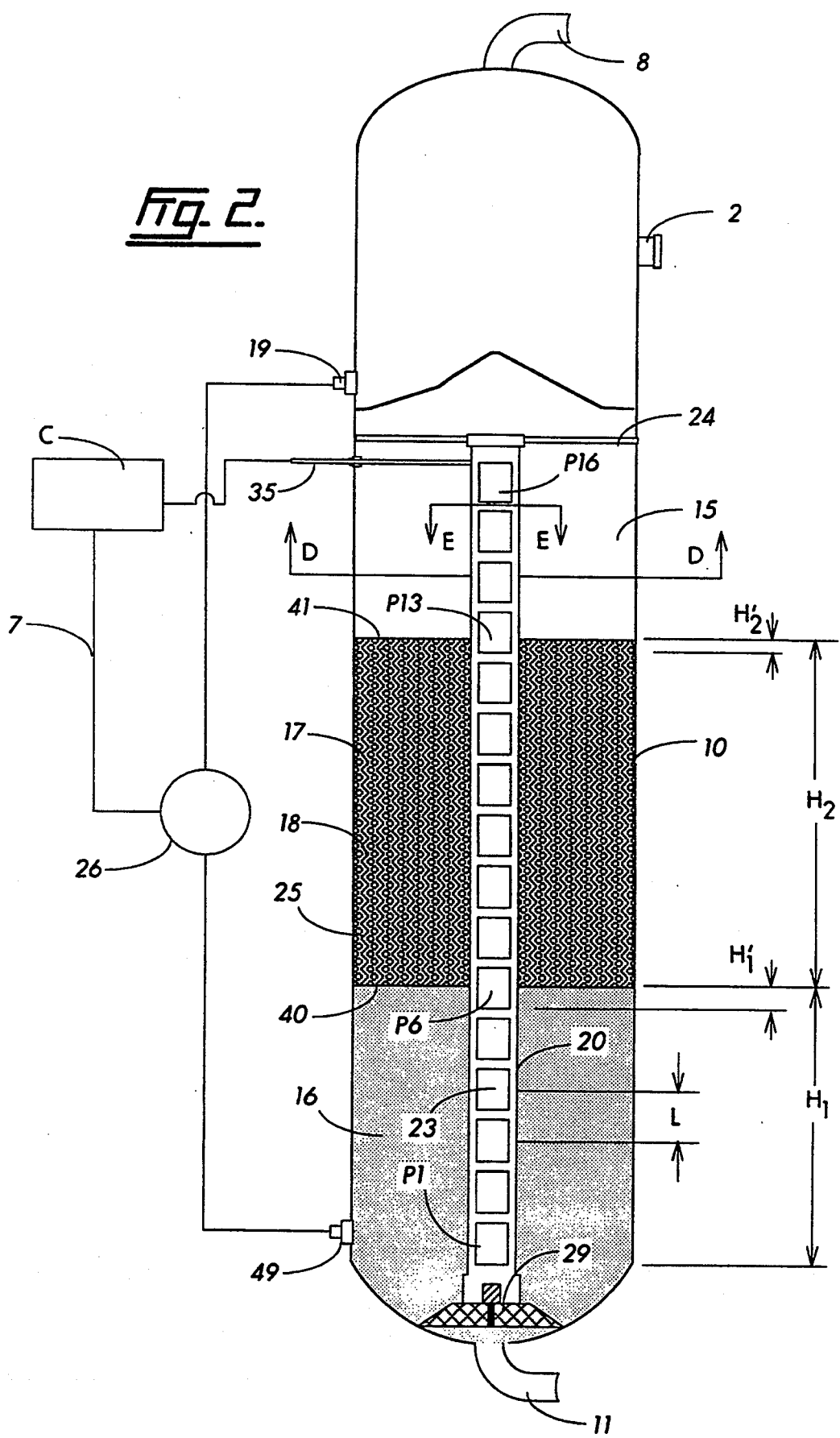
FIG. 2 is a fanciful sectional side view showing the separator vessel with the capacitance probe assembly in association therewith, said vessel containing a batch of production fluid which has separated into free water, gassy emulsion, and gas layers.

The components of the batch 10 separate in the chamber 5, as shown in FIG. 2, to form a bottom layer 16 of free water, an intermediate layer 17 of gassy emulsion, and a top layer 15 of free gas.

A differential pressure transducer 26 is associated with the vessel 1. The transducer 26 comprises a first sensor 49 at the base of the liquid-containing column 18 (formed by free water and emulsion layers 16, 17) and a second sensor 19 in the gas layer 15. The differential pressure transducer 26 is adapted to monitor the increasing head of the fluid column 18 and emit signals indicative of the fluid head's magnitude. The output of the differential pressure transducer 26 is fed to the microprocessor C.

As shown in FIG. 5, during the accumulation of a batch, the dump valve 12 is closed and the fill valve 3 is open. When the head of the liquid-containing column 18 reaches a pre-determined high value, the microprocessor C signals inlet valve 3 to close. The dump valve 12 is signalled to open by the microprocessor C when the fluid column is stabilized. The backpressure in the vessel chamber 5 then functions to quickly discharge part of the column 18 through underflow line 11. When the head of the column 18 diminishes to a pre-determined low value, the microprocessor C acts to close the dump valve 12. The sequence is schematically illustrated in FIG. 5.

The microprocessor C is suitably connected and programmed to process the signals indicative of the gas flow, the mass of each fluid dump, and the time involved.

In summary then:
  the separator functions to separate most of the gas from the liquid;
  the separator operates on a batch basis;
  a liquid-containing column 18 having two layers, one being free water 16 and the other being gassy emulsion 17, is generated;
  the quantity of free gas 15 passing through the vessel is measured and the results are collected by the microprocessor;
  the total mass of liquid-containing fluid passing through the underflow line 11 is measured and the results are collected by the microprocessor; and
  the time is recorded by the microprocessor.

Figure 3:
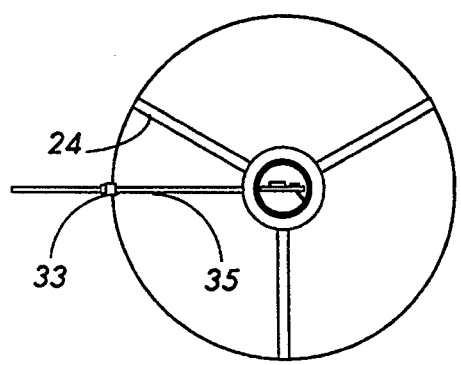
FIG. 3 is an end view along the line D—D of FIG. 2.
Figure 4:
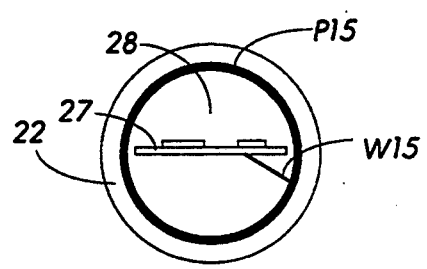
FIG. 4 is an end view along the line E—E of FIG. 2.

Turning now to the capacitance probe assembly B, as shown in FIGS. 2, 3, 4, it includes a capacitance probe 20, a yoke 24 supporting the probe 20, a signal wire conduit 35 for connecting the probe 20 with the microprocessor C, a packoff 33 for sealing the conduit 35 to the wall of the vessel 1, a restraint 29 for centering the probe 20 in the vessel chamber 5, and a circuit board 27 for actuating the assembly B.

More particularly, as shown in FIGS. 2, 3, 4, the probe 20 comprises a linear array 23 of sixteen active plates P1-P16 mounted in an electrically insulating probe shell 22, which is suspended vertically in the vessel contents by the supporting yoke 24. By "electrically insulating", the meaning thereof will be understood by capacitance probe designers that the shell is made from a dielectric material so that the plates are capacitance coupled to the fluid but resistively insulated from the fluid. The dielectric selected should, of course, be chemically resistant to the fluid, examples thereof including but not limited to: Teflon, ceramic materials, and preferably fiberglass-reinforced epoxy, e.g., Bondstrand. The active plates P1-P16, generally any conductor, preferably aluminum are capacitively coupled by the shell 22 and the fluid in the vessel chamber 5 to a common return plate 25 which, in the embodiment shown, is the wall of the vessel 1. The vessel wall, generally any conductor, for example, mild steel, is optionally coated on the interior side with a substance which will prevent corrosion, e.g., an epoxy coating.

For purposes of terminology, the capacitance probe assembly B, when associated with the return plate 25, forms a capacitive assembly.

In the case of applicant's prototype, the following details applied:
  vertical length of vessel=7'9"
  vertical length of probe=4'6"
  number of active plates=16
  size of active plates=2"×2" OD
  spacing of active plates from vessel wall=5"
  spacing of active cylindrical plates, center to center=2½"

Figure 6:
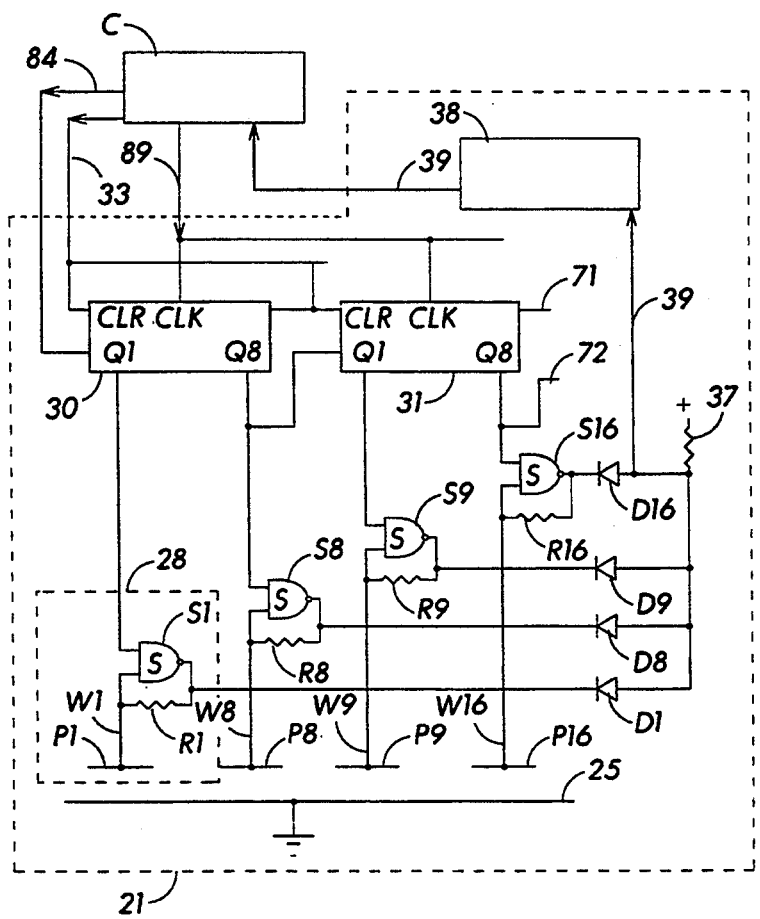
FIG. 6 is a diagram showing the preferred probe circuit, involving discrete relaxation oscillator circuits for charging the active plates and being adapted to eliminate parasitic capacitance and to provide for multiplexing of the oscillator outputs.

As shown in FIG. 6, an electronic circuit 21 is provided for activating the plates P1-P16 and transmitting the frequency signals generated, which are indicative of the dielectric constant of the fluid being tested, to the microprocessor C for analysis. The circuit 21, forming part of the probe 20, is designed to minimize parasitic capacitance. In this respect, an individual oscillator circuit 28, for charging and discharging an associated active plate, is mounted close to each such active plate P1-P16. Means are provided for energizing and for selectively and individually enabling the discrete oscillator circuits 28.

More particularly, in the preferred embodiment shown, the circuit 21, FIG. 6, comprises sixteen separate or discrete relaxation oscillator circuits 28. Each of the oscillator circuits 28 is mounted on the printed circuit board 27, FIG. 4, which is centered in one of the sixteen, vertically and linearly arranged, cylindrical active plates P1-P16.

Each oscillator circuit 28 comprises a dual input Schmidt NAND gate S1-S16 connected with a feedback resistor R1-R16. The active plate P1-P16 is connected by a short conductor W1-W16 to an input of the Schmidt NAND gate S1-S16.

The oscillator circuits 28 are sequentially and individually enabled by a logical high applied to one of the dual inputs of the Schmidt NAND gates S1-S16 by one of the outputs Q1-Q8 of two serial-to-parallel shift registers 30, 31 operatively controlled by microprocessor C. The outputs of the shift registers 30, 31 are initially cleared on set-up by clocking in sufficient consecutive zeros into the first shift register 30 or by the correct toggle of the clear line 33. The data line 84 is held high by the microprocessor C while the clock line 33 is toggled, thereby raising $Q_1$ of the shift register 30, enabling the oscillator circuit 28, connected to $P_1$, subsequent toggles of the clock, which will enable the next oscillator circuit 28. The outputs of non-selected oscillator circuits 28 will be at a logical one.

Sixteen blocking diodes D1-D16 are provided for transferring the output signal from an enabled oscillator circuit and for blocking the signal from reaching non-enabled oscillator circuits. More particularly, each diode D1–D16 is connected to the output of one of the Schmidt NAND gates S1–S16. The anodes of the diodes D1–D16 are connected to a pull up resistor 37 and the input to a frequency divider 38. The diodes D1–D16 and resistor 37 cooperate to allow a selected oscillator circuit 28 to output its frequency signal to the input of the frequency divider 38.

The frequency signal is dependent on the dielectric value of the fluid between the active plate P1–P16 involved and the return plate 25. The frequency divider 38 conditions the signal frequency to a lower frequency by dividing the frequency before it is transmitted out of the probe 20 by the output conductor 39 to the microprocessor C, for analysis.

As described, we have chosen to enable the oscillator circuits 28 in a sequence and to then collect the signals from the oscillator circuits 28 as they are activated. However it is contemplated that alternatively all of the oscillator circuits could be enabled continuously and their output signals multiplexed.

Figure 7:
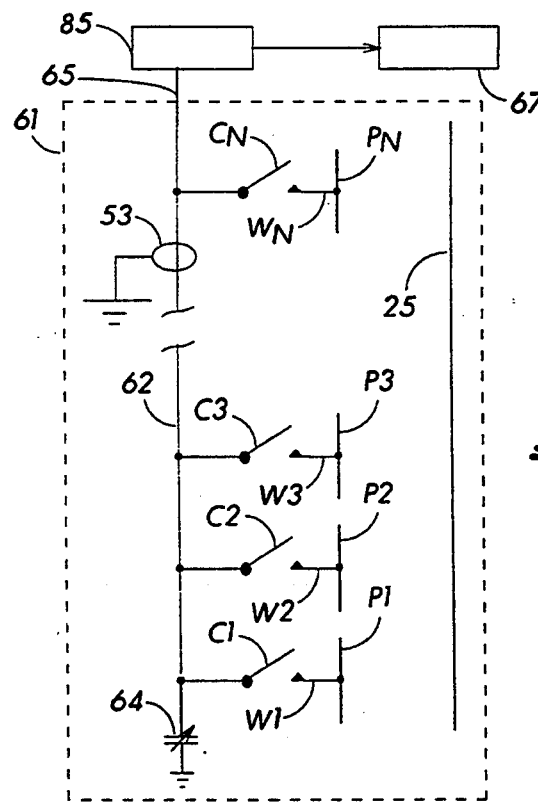
FIG. 7 is a diagram showing an alternative probe circuit.

As described, individual oscillator circuits 28 are placed adjacent or near to each active plate P1–P16 in order to eliminate the effects of parasitic capacitance. However it is contemplated that alternatively a single oscillator or other such electronic circuit capable of measuring capacitance could be utilized and the effects of the parasitic capacitance minimized by other means such as the use of switching devices adjacent to, or at, the active plates. A circuit 61 to accomplish this end is disclosed in FIG. 7.

The circuit 61 comprises an electronic capacitance measuring circuit 85 and a microprocessor 67. The circuit 61 is connected to the probe 20 by a coaxial cable 65 having a center lead 62 and a shield 53. The center lead 62 is connected to one contact of the switches C1–Cn. Each switch C1–Cn is located adjacent an active plate P1–Pn and is connected thereto by a short conductor W1–Wn. The capacitance of the coaxial cable 65 (represented by variable capacitor 64) can be measured with all of the switches C1–Cn open and this reading is subtracted from the individual readings obtained when each plate P1–Pn is sequentially activated to measure the capacitance between the selected plate and the common return plate 25. The switches C1–Cn are sequentially closed normally under control of the microprocessor 67. The switches C1–Cn can be either of a solid state nature, an electro-mechanical device, or a mechanical device. Any interface circuits required to control the switching devices are dependent upon the switching device chosen and are well understood by those skilled in the art.

In the use of the system, the capacitance probe 20 is positioned in the vessel chamber 5 so that it will extend downwardly sufficiently to intersect the emulsion/free water and gas/emulsion interfaces 40, 41.

Figure 5D:
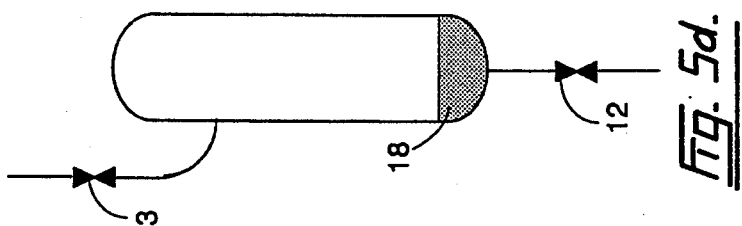
FIGS. 5a-5d show a schematic of the separator in simplified form, showing the steps in the operational sequence of accumulating the batch, recording the readings on the accumulated batch, dumping the batch, and recording the empty readings.
Figure 5C:
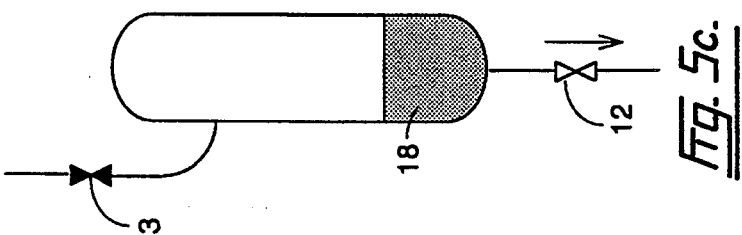
Figure 5B:
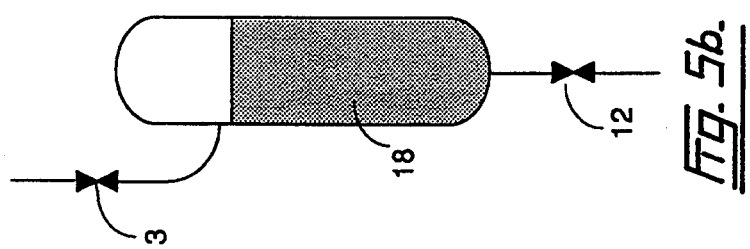
Figure 5A:
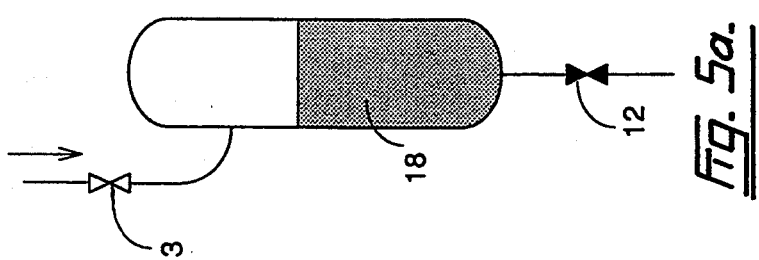

The microprocessor C is programmed to:
open the feed line inlet valve 3 and close the dump valve 12, as illustrated in FIG. 5a, to initiate accumulation of a batch and to monitor the head until a batch has been accumulated;
close the feed line valve 3 and to instruct the shift registers 30, 31 to commence sequentially enabling each of the oscillator circuits 28 and their respective active plates P1–P16, to determine the dielectric constant profile of the accumulated batch;
open the dump valve 12, as illustrated in FIG. 5c, and monitor the head until the batch has been dumped;
close the dump valve 12, as illustrated in FIG. 5d, and monitor the head until it is stable and determine the dielectric profile of the fluid remaining; and
process the readings of the gas meter 8a.

During the steps shown in FIGS. 5b and 5d, during which the batch is held, the microprocessor C is programmed to read the differential pressure transducer 26 and obtain a measure of $h_3$, i.e. the total head which is contributed by the layers 16 and 17 of free water and emulsion, as shown in FIG. 2.

The microprocessor C is further programmed to compare the frequency readings due to capacitance of the feed stock, as seen by plates P1–P16, to determine the heights at which the readings changed markedly, thereby identifying and locating the interfaces 40 and 41. For example, the microprocessor C determines which plates of linear array 23 are below the emulsion/free water interface 40, which plates are below the gas/emulsion interface 41, and which plates of array 23 are intersected by the interfaces 40, 41. The microprocessor C then uses the following relationship to determine the heights $H_1'$ and $H_2'$ of the interfaces on the particular plates that are intersected:

$$H_2' = \frac{L(R - R_{GAS})}{R_E}$$

where
$R_{GAS}$ = Reading 100% gas, a program constant
L = module length, a program constant
$R_E$ = average reading of the plates that are totally between the gas/emulsion and emulsion/free-water interface.
R = reading a function of capacitance feed stock similarly $$H_1' = \frac{L(R - R_E)}{R_{H2O}}$$

where
$R_{H2O}$ = reading for 100% formation water, a program constant

As shown in FIG. 3, the microprocessor C then calculates the heads $H_1$ and $H_2$ of the free water and emulsion layers respectively, using the following relationships:
$H_1 = (N_1 \times L) + H_1'$ where
$N_1$ = the number of plates below interface 40
$H_1'$ = height of interface 40 on plate P6
and
$H_2 = (N_2 \times L) - H_1 + H_2'$
where
$N_2$ = the number of plates below interface 41
$H_2'$ = the height of interface 41 on plate P13

The head ($h_E$) due to the emulsion may be calculated using the relationship:
$h_E = h_3 - (H_1 \times SG_W)$
where
$h_E$ = head of emulsion
$h_3$ = the total head of the emulsion and free water as measured by the differential pressure transducer 26
where
$SG_W$ = known specific gravity of formation free water, a program constant.

The specific gravity of the emulsion ($SG_E$) may then be calculated using the relationship:

$$SG_E = h_E/h_2$$

Having the specific gravity of the emulsion and the capacitance value for each of the plates P1–P16, the microprocessor C may calculate the oil/water ratio of the emulsion extending between a plate of array 23 and the return plate 25. The microprocessor C may then average the oil/water ratios for the plates of array 23 in the emulsion layer 17 and determine a value. indicative of the overall oil/water ratio for the layer.

More particularly, the readings associated with each plate of array 23 of the probe 20 are scaled by the microprocessor C in order to accommodate the end point and span variations in accordance with the relationship. Other known mathematical techniques to compensate for end point and span variations can be used.

$$R = S_R$$

where $$S_R = \left(\frac{\omega - \omega_{oil}}{\omega_{H2O} - \omega_{oil}}\right) N$$

where
$S_R$ = scaled reading
$\omega_{oil}$ = unscaled reading for 100% oil (formation), a program constant for the particular plate
$\omega_{H2O}$ = unscaled reading for 100% water (formation) a program constant for the particular plate
$\omega$ = unscaled reading for the particular plate
N = scaler quantity desired for 100% water scaled reading, a program constant The dielectric constants of gas and oil are small when compared to that of water. The microprocessor C therefore may calculate as a first approximation the volumetric ratio $C_v$ of water in the gassy emulsion in accordance with the relationship:

$$C_V = f(S_R)$$

This relationship was experimentally established for a given probe design. For example. in one instance, it was found to be:
$C_V = 1.50 + 1.21\, S_R + 0.0057\, S_R^2$
and
$V_w = C_v[V_E] = C_v[V_G + V_O + V_W]$
where
$V_W$ = volume of water in emulsion
$C_V$ = volume ratio of water in gassy emulsion
$V_E$ = volume of emulsion
$V_G$ = volume of gas
$V_O$ = volume of oil
and $$V_G = V_E - \left[\frac{(h_E \times A - V_W)}{SG_O} + \frac{V_W}{SG_W}\right]$$

A = cross sectional area of vessel cross sectional of probe, a program constant
where:
$SG_O$ = known specific gravity of the formation oil, a program constant.

The scaled reading is then corrected to account for the entrained gas and used to obtain the mass cut of the emulsion in accordance with:
$C_R$ = corrected reading
$C_R = S_R + (N_G + C_F)$
where:
$C_F = V_G/V_E$
$N_G$ = scaled reading for gas 100%, a program constant
Then the mass cut $C_M$ can be calculated as follows:
$C_M = f(C_R) \times SG_W/SG_E$
where: $f(C_R) = f(C_V)$ The prototype assembly described was tested by passing a production stream of gassy emulsion separately through it and comparing the calculated water cuts against centrifuged water cuts, with the following results:

TABLE 1

| Well | Spun Cut | Calculated Cut | Difference |
|---|---|---|---|
| Well 9–16 | 46% | 44.5% | −1.5% |
| | 46% | 45.8% | −0.2% |
| | 48% | 46.7% | −1.3% |
| | 46% | 45.7% | −0.3% |

The calculated cuts were the average cut readings of all of the plates covered by the emulsion whereas the spun cuts were obtained from small samples of the emulsion. The samples from Well 3B13 contained water droplets mixed in the emulsion. It is believed that the higher calculated cut readings for Well 3B13 are a result of the probe accounting for these water droplets, which were not accounted for with the spun cuts as they had separated from the emulsion prior to being spun.

The embodiments of the invention in which an exclusive property or privilege is claimed are defined as follows:

1. A two terminal type capacitance probe assembly, adapted to be capacitatively coupled with a return plate means by a fluid under analysis, comprising:
   (a) a generally linear array of discrete active plates mounted within a shell made from a dielectric material so that the plates are capacitance coupled to the fluid but are resistively insulated from the fluid;
   (b) a plurality of discrete oscillator circuits;
   (c) means for energizing the oscillator circuits;
   (d) each oscillator circuit being individually and permanently connected to an active plate for directly charging and discharging that active plate so that the frequency of the applied potential varies with the dielectric constant of the fluid extending between that active plate, which is a first terminal of the assembly, and the return plate means, which is the second terminal, to produce variable frequency signals indicative of said dielectric constant;
   (e) means for selectively and individually enabling an oscillator circuit; and
   (f) means for collecting the individual signals produced by the oscillator circuits and determining for each signal a value indicative of the dielectric constant of the fluid extending between the active plate involved and the return plate means.

2. The assembly according to claim 1 wherein the means (f) comprises.:
   means for blocking the output signal from the enabled oscillator circuit from the outputs of the non-enabled oscillator circuits;
   means for conditioning the output signal from an enabled oscillator circuit to a lower frequency; and a microprocessor operatively controlling means (e) and connected to receive the output from the conditioning means and to determine the values indicative of dielectric constant.

3. The assembly according to claim 1 wherein:

each oscillator circuit is a relaxation oscillator circuit;

the oscillator circuits are mounted in the shell close to the active plates; and the number of oscillator circuits is equal to the number of active plates and each active plate is connected with one oscillator circuit.

4. The assembly according to claim 2 wherein:

each oscillator circuit is a relaxation oscillator circuit;

the oscillator circuits are mounted in the shell close to the active plates; and the number of oscillator circuits is equal to the number of active plates and each active plate is connected with one oscillator circuit.

* * * * *